United States Patent [19]

Kegel

[11] 4,203,450

[45] May 20, 1980

[54] APPARATUS FOR MONITORING AND INDICATING THE ONSET OF PARTURITION

[76] Inventor: Werner Kegel, 4543 Lienen Hoeste 45, Fed. Rep. of Germany

[21] Appl. No.: 898,245

[22] Filed: Apr. 20, 1978

[30] Foreign Application Priority Data

May 3, 1977 [DE] Fed. Rep. of Germany ....... 2719698

[51] Int. Cl.[2] ............ A61B 5/00

[52] U.S. Cl. ............ 128/630

[58] Field of Search .............. 128/2 R, 2 S, 2 H, 2 N, 128/2.1 A, 630, 632, 736, 738, 903

[56] References Cited

U.S. PATENT DOCUMENTS

| | | | |
|---|---|---|---|
| 2,812,757 | 11/1957 | Lusk et al. | 128/2 R |
| 3,572,316 | 3/1971 | Vogelman et al. | 128/2.1 A |
| 3,805,796 | 4/1974 | Terry, Jr. et al. | 128/419 PG |
| 3,844,273 | 10/1974 | Polson | 128/2 R |
| 4,028,687 | 6/1977 | Hamaguchi et al. | 128/2 R |
| 4,055,839 | 10/1977 | Skeggs | 128/2 S |

*Primary Examiner*—William E. Kamm

*Attorney, Agent, or Firm*—Jordan and Hamburg

[57] ABSTRACT

An apparatus for warning a breeder that one of his animals is about to give birth has a harness which mounts an electrical resistance sweat detector and a transmitter responsive thereto on the neck of the expectant animal; detection of an increase in sweating which precedes parturition is accompanied by the transmission of a pulse coded radio signal which is picked up by a remote receiver tuned to respond just to that coded signal, and the receiver then activates a visual or audible warning to alert the breeder to the approach of parturition.

10 Claims, 3 Drawing Figures

Fig. 1
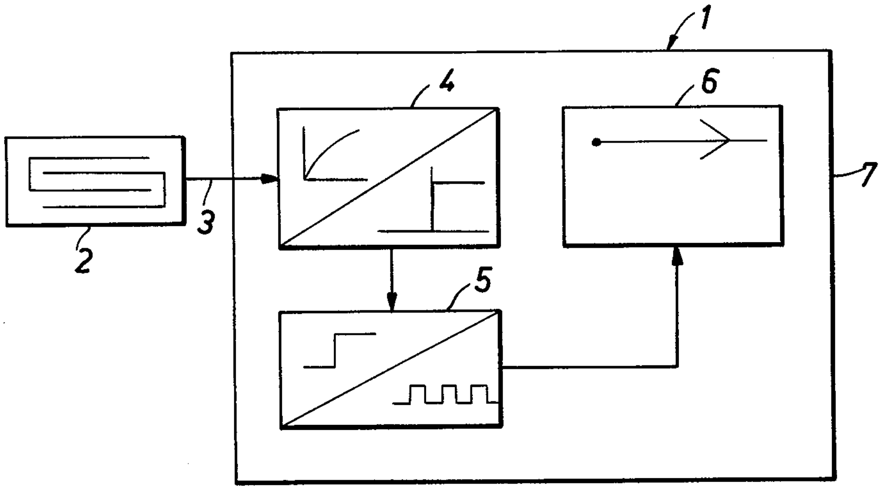
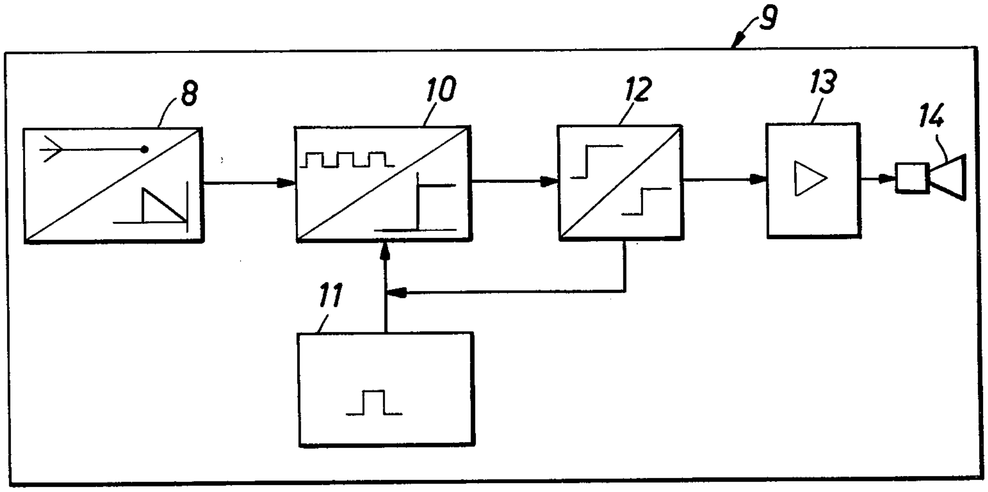
Fig. 2

APPARATUS FOR MONITORING AND INDICATING THE ONSET OF PARTURITION

The invention relates to an apparatus for monitoring and indicating the onset of parturition in animals such as horses and cows.

More particularly, the invention relates to such apparatus which comprises a measured-value pick-up responding to a change in state of the body of the expectant animal a signal generator in the form of a transmitter and a signal-actuated indicating device for giving an optical and/or acoustic warning signal.

Apparatuses of this kind are intended to free breeders or owners of an expectant mother animal, e.g. a mare, from the necessity of constantly watching the mare ready for foaling over long periods of time before the expected onset of parturition or birth, in order to be present at the beginning of the birth and during parturition, and on the other hand to warn the breeder or owner in sufficient time for him to attend the birth and to intervene with help as soon as any disturbances or difficulties occur in the course of the birth or immediately afterwards. This is of particular importance with mares of high value, because an abortion involves heavy loss, which is increased substantially if the mare is injured or even dies. Not infrequently, even when a birth takes place normally, it is observed that a foal which is otherwise healthy in itself suffocates in the bag of waters because the latter does not open after the birth and normal breathing of the foal does not occur. A known apparatus disclosed in DT-OS No. 24 16 829 aims at detecting changes in shape of the genital passages for example swelling of the vagina or opening of the labia of the vulva, or of other organs, for example the swelling of the udder, by means of an electrical switch, actuation of which causes and alarm device to be switched on. The alarm deivce, which may deliver an acoustic or an optical alarm signal, may also be switched on by a transmitter which transmits a signal passed by the switch. The switch mounted on the animal and responding to changes in shape may be united with the transmitter or be connected thereto by means of electrical leads. In addition to such a switch, for safety reasons relating to the reliable production of a warning signal, another switch may be provided which detects another specific change in the body of the expectant mother animal and is connected in series with the first switch, for example, so that a warning signal is only given if both switches are actuated in response to onset of parturition.

The structural development of such an apparatus is comparatively complicated and expensive. In particular, however, the correct fitting of such switches is an operation which is not simple and presupposes expert knowledge to prevent false alarms arising from incorrect fitting of the switches, or to prevent a warning signal given too late or not at all. The mounting of switches in the vagina, in front of its outlet and so on is also disturbing during the birth process and in addition is not without danger, at least with horses which react particularly sensitively to even weak electric shocks which may accompany an electrical defect occurring for example as a result of damage to the equipment. Finally, the detection of changes in shape or organs associated with the birth does not offer the requied reliability of giving a warning signal in good time. For example, detecting the swelling of the udder is unsatisfactory because the swelling may occur a considerable time before the actual birth. Actuation of a switch by an expulsion process from the vagina or parting of the labia of the vulva by the foal forcing its way out leads to a warning signal being given only at a moment when the birth is already in progress. Bearing in mind that a supervisor may be in another building, and at night may first have to dress before he can make his way to the foaling box, then it is clear that despite the supervisor reacting immediately to a warning signal, he may, in some circumstances, reach the foaling box too late to intervene with help or to open the bag of waters which must be done immediately after foaling in order to avoid injury to the foal or its death. It must also be borne in mind that multipara mares often foal very rapidly because a way has already been prepared through the genital passages.

These problems also arise in another known apparatus which is disclosed in DT-OS No. 22 14 221, wherein, apart from a mechanically actuated switch which responds to changes in shape, it is also proposed to use a measured-value pick-up which switches over depending on temperature and then energizes a transmitter. The temperature of horses, particularly expentant mares, is a quantity which can change very easily, for example if the mare is excited for reasons not connected with the birth, and is therefore ill-suited for monitoring the beginning of a birth reliably. An apparatus which reacts depending on temperature is therefore unreliable with all the resulting consequences.

In each above-mentioned apparatus, the reliability of producing a warning signal is also further reduced by the fact that not only the signal from the transmitter, but also signals from other equipment which transmit on the same wavelength, may excite the receiving section of the indicating device. Other equipment capable of this include, for example, amateur radio sets and, in particular, vacuum cleaners, kitchen equipment and other general and domestic electrical equipment which, possibly as a result of inadequate suppression, transmit interference which is picked up by the receiving section of the indicating device as a control or actuating signal. Devices which deliver disturbing interference are used in considerable numbers on farms and in breeding enterprises, while emissions from amateur radio or radio-telephone devices carry over considerable distances, so that spurious signals from these can arrive from a wide area.

An object of the invention is to provide an apparatus capable of detecting the onset of a birth reliably and in good time and ensures a warning signal is given only when the change in state in question of the mother animal has been determined.

According to the invention there is provided apparatus for monitoring and indicating the onset of parturition in animals such as horses, comprising means responsive to a sweat-inducing change in state occurring in the body of an expectant animal at the onset of parturition, said means including a measured value pick-up detecting element for contact with the skin or coat of the animal which produces a signal depending on sweat humidity secreted by the animal, signal transmitting means comprising a limiting value transmission means coupled to the detecting element to receive said signal therefrom, and a code signal generating transmitter controlled by said limiting value transmission means for producing a transmitted coded signal indicative of onset of parturition, and a parturition indicator including signal receiving means tuned to the code signal generating transmitter and means controlled by the signal receiving means for providing a warning of the onset of parturition.

The apparatus according to the invention determines the sweat humidity of the mother animal and accordingly works depending on a change in state which, it has been found, precedes a birth particularly reliably and regularly. Such a secretion of sweat occurs in particular at the neck of the mother animal, and if it reaches a certian amount and lasts over a certian period of time, is a reliable indication and, moreover appears early enough before the actual foaling process that a supervisor still has sufficient time, after receiving a warning signal, to reach the foaling box and attend the birth. The limiting-value transmission means associated with the detecting element can ensure that the signal generator, i.e. the transmitter, is only activated when persistent sweat secretion, characteristic of the beginning of the birth process, occurs. By adjusting the limiting value transmission means, the apparatus can be adapted to different reactions of the mother animal. The use of a transmitter in the from of a code-signal generator, in conjunction with a signal receiving means tuned to the code signal, ensures that only signals from the transmitter and not any spurious signals which may happen to be on the same wavelength are able to actuate the parturition indicator warning device.

Fitting the apparatus to the mother animal can be carried out by anyone without any expert knowledge and the apparatus can be located at a point which in no way hampers the birth. In this connection, a further development of the invention provides that the detecting element is connected through conductors to the transmitter, which is encapsulated in a shockprook housing, and a harness of straps is provided to hold the housing in front of the shoulder-blade of the mother animal and the detecting element against the neck of the mother animal. The harness may comprise a surcingle, known per se, a neck strap which is connected to the surcingle through elastic webbing in use disposed in the region of the withers in the back region of the mother animal, the said strap carrying the detecting element at its inside for contact with the neck of the animal, and a holding strap which is taken between the front legs of the mother animal from the belly side of the surcingle to a carrier plate for the housing. The neck strap is connected to the housing in the region of the underside of the neck of the mother animal.

This construction renders it possible to fit the measuring and transmitting section to the mother animal in a normally safe position relieved of the effects of shocks or blows even in the event of violent movements by the animal. The neck strap aided by initial tension in the elastic webbing ensures that the detecting element bears reliably against the neck of the mother animal without freedom of movement of the animal being in any way hampered. The mother animal is not exposed to harmful constraints in any region which might distrub the required restful nerves of the animal. Above all, however, reliable location is possible without constricting any region of the animal and hampering the free flow of blood. In particular, the rear region of the metacarpus and the hindquarters including the extremities remain free from any attachment means.

The invention will be described in more detail by way of example only with reference to the accompanying drawings, in which:

FIG. 1 shows a diagrammatic illustration of the measured-value pick-up and transmitter according to the invention;

FIG. 2 is an illustration similar to FIG. 1 of the indicating device; and

Figure 3:
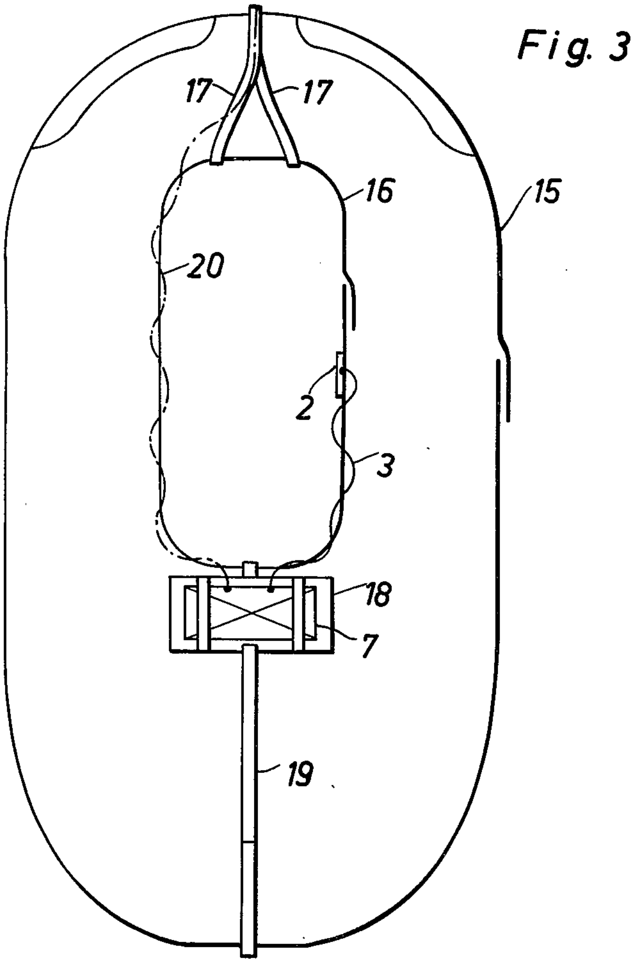
FIG. 3 is a diagrammatic illustration of the strap harness for locating the apparatus on a mother animal.

The apparatus illustrated in FIGS. 1 and 2 comprises a measuring and transmitting section 1, consisting of a detecting element 2 which, in the example illustrated, is constructed so as to alter its electrical resistance depending on the sweat humidity of a mother animal. The detecting element 2 is connected, through electrical conductors 3, to a limiting-value transmitter 4 which, when a predetermined limiting value for a change in resistance at the detecting element 2 is exceeded, controls a timing generator 5 in the form of a multivibrator or digital filter. This timing generator 5 switches a transmitter 6 on and off in a predetermined timing sequence which accordingly transmits a code signal, in the form of pulses following one another at specific intervals of time and with a specific duration, that is a pulsed code signal if a specific mark-to-space ratio. According to the code, the number of pulses may amount to 7/sec for example. The components 4, 5 and 6 are accommodated in a shockproof housing 7 in which there is a chargeable accumulator, not illustrated, as an energy source.

The transmitted code signal from the transmitter 6 is picked up by a remote receiving section 8 of the indicating device 9 and is reproduced at its output unaltered in frequency. The receiving section 8 of the indicating device 9 is connected to a pulse counter 10 which receives the time-coded output signal and adds up its pulses. Coupled to the pulse counter 10 is a timing element 11, for example in the form of a multivibrator, which sets the pulse counter back to "O" at fixed intervals of time. The pulse counter 10 comprises a comparator circuit which, on coincidence between the pulses counted per unit of time from the receiving section 8 and the predetermined number of pulses according to the code, delivers a release signal to a switching amplifier 12 which comprises a self-holding circuit that is resettable by hand. Therefore, as soon as the switching amplifier 12 receives the release signal from the pulse counter 10, the switching amplifer becomes and remains activated and actuates an acoustic and/or optical warning-signal transmitter 14 for example through a further amplifier 13. The indicating device 9, may be located anywhere within the transmission range of the transmitter, may be adapted to be carried by the supervisor, and can be used for a plurality of measured-value pick-up/signal transmitter units.

Fitting of the measuring and transmitting section of the apparatus to a mother animal approaching a birth is effected by means of a harness which is illustrated diagrammatically in FIG. 3. In detail, this harness comprises a surcingle 15 which is placed close behind the withers of a mother animal, round its body, and is gently pulled tight. The harness has a neck strap 16 which is fitted close to the neck projection of the mother animal, i.e. the root of the neck, and is adjusted to the width of the neck. Connected to the upper region of the neck strap 16, is elastic webbing 17 which extends at both sides of the withers and unites behind these and also acts on the back region of the surcingle 15. In the region of the underside of the neck of a mother animal, the neck strap is secured to a carrier plate 18, preferably of leather, for the housing 7. The latter is located in front of the shoulder-blade of the mother animal. Also secured to the underside of the carrier plate 18 is a holding strap 19, which is adjustable in length and is led between the front legs of the mother animal to the belly side of the surcingle.

To the inside of the neck strap 16 is secured the detecting element 2, and the neck strap 16 forms a holding and guiding means for the conductors 3, leading to the limiting-value transmitter in the housing 7. The neck strap 16 also forms a guide and holding means for a transmission-aerial wire, which is illustrated in chain line and which is taken up from the transmitter 6 in the housing 7 to the region of the elastic webbing 17. The aerial wire is positioned on the opposite side of the animal's neck from the detecting element. The detecting element 2 is constantly urged against the surface of the skin or the coat of the mother animal in the region of the neck projection by the neck strap 16 which position is maintained through the action of the tensioned elastic webbing 17 which holds the neck strap 16 constantly under bearing tension.

I claim:

1. Apparatus for monitoring and indicating the onset of parturition in animals such as horses, comprising means responsive to a sweat-inducing change in state occurring in the body of an expectant animal at the onset of parturition, said means including a measured value pick-up detecting element for contact with the skin or coat of the animal which produces a signal depending on sweat humidity secreted by the animal, signal transmitting means comprising a limiting value transmission means coupled to the detecting element to receive said signal therefrom, and a code signal generating transmitter controlled by said limiting value transmission means for producing a transmitted coded signal indicative of onset of parturition, and a parturition indicator including signal receiving means tuned to the code signal generating transmitter and means controlled by the signal receiving means for providing a warning of the onset of parturition.

2. An apparatus as claimed in claim 1, in which the limiting value transmission means comprises a signal generator for producing a transmitter-controlling signal when the signal from said detecting element exceeds a predetermined value.

3. An apparatus as claimed in claim 1 in which the detecting element comprises a resistive measuring element electrical resistance of which changes depending on the sweat humidity.

4. An apparatus as claimed in claim 1, in which the limiting-value transmission means is connected to a timing generator associated with the transmitter for switching the transmitter on and off to produce the coded signal in a predetermined timing sequence.

5. Apparatus as claimed in claim 4, in which said generator is a multivibrator.

6. An apparatus as claimed in claim 4 in which the signal receiving means includes means for reproducing the coded signal received from the transmitter, a pulse counter which comprises a comparator circuit, and a resettable timing means, said comparator circuit on coincidence between the pulses counted per unit of time and the number of pulses according to the code, delivering an activating signal to the warning means of the parturition indicator.

7. An apparatus as claimed in claim 6, in which there is a manually resettable self-holding circuit coupled to the comparator for storing the said release signal.

8. An apparatus as claimed in claim 1 in which the detecting element is separate from the signal transmitting means and is connected through conductors thereto, there being a shockproof housing encapsulating the signal transmitting means, and a harness is provided to hold the housing in front of the shoulder-blade of the animal and the detecting element against the neck of the animal.

9. An apparatus as claimed in claim 8, in which the harness comprises a surcingle, a neck strap, elastic webbing connecting the neck strap to the surcingle, the elastic webbing in use being disposed in the region of the withers in the back region of the animal, the neck strap mounting the detecting element at its inside, and also mounting the housing, there being a holding strap interconnecting a belly side of the surcingle and the housing.

10. An apparatus as claimed in claim 9, in which the neck strap forms holding means for the conductors leading from the detecting element and for a transmission-aerial wire leading from the transmitter in the housing to the region of the elastic webbing.

* * * * *